US008353706B2

(12) United States Patent
Kay

(10) Patent No.: US 8,353,706 B2
(45) Date of Patent: Jan. 15, 2013

(54) BREATHING APPARATUS SIMULATOR

(75) Inventor: Michael B. Kay, Round Lake Beach, IL (US)

(73) Assignee: Ocenco, Inc., Pleasant Prairei, WI (US)

(*) Notice: Subject to any disclaimer, the term of this patent is extended or adjusted under 35 U.S.C. 154(b) by 1008 days.

(21) Appl. No.: 12/016,604

(22) Filed: Jan. 18, 2008

(65) Prior Publication Data
US 2008/0176200 A1 Jul. 24, 2008

Related U.S. Application Data

(60) Provisional application No. 60/885,821, filed on Jan. 19, 2007.

(51) Int. Cl.
G09B 23/28 (2006.01)
(52) U.S. Cl. .............. 434/265; 434/262; 128/201.13; 128/202.26; 128/205.27
(58) Field of Classification Search .............. 434/262, 434/265; 128/201.13, 202.26, 205.27
See application file for complete search history.

(56) References Cited

U.S. PATENT DOCUMENTS

| 3,226,681 A | | 12/1965 | Gluckstein |
| 3,625,866 A | * | 12/1971 | Conde ............................. 502/68 |
| 3,908,649 A | * | 9/1975 | Eckstein ................ 128/201.13 |
| 3,935,252 A | * | 1/1976 | Tomomatsu ................ 568/617 |
| 4,325,364 A | | 4/1982 | Evans et al. |
| 5,186,165 A | * | 2/1993 | Swann ...................... 128/201.28 |
| 5,394,867 A | * | 3/1995 | Swann ...................... 128/201.25 |
| 5,524,616 A | * | 6/1996 | Smith et al. .............. 128/205.27 |
| 5,937,856 A | | 8/1999 | Jonasson et al. |
| 6,880,557 B2 | * | 4/2005 | Downey .................... 128/205.28 |
| 2007/0215159 A1 | * | 9/2007 | Ross et al. ............... 128/205.28 |
| 2008/0085498 A1 | | 4/2008 | Wezurek et al. |

FOREIGN PATENT DOCUMENTS

| DE | 10 2006 044 | 9/2007 |
| GB | 2 169 810 | 7/1986 |

OTHER PUBLICATIONS

CSE "Safety Products to Live by," available on the internet as early as May 2, 2007 (3 pages).
Drägersafety Press Release "Draeger's New Oxy K Plus Training Simulator Provides Realistic Self-Contained Self-Rescuer (SCSR) Training," dated May 23, 2007 (2 pages).
Jones et al., "Use of Self-Rescuers in Hot and Humid Mines," published 2003, Mines Rescue Service Limited, pp. 1-70.
International Search Report for International Application No. PCT/US2008/051435, dated May 21, 2008.
Written Opinion for International Application No. PCT/US2008/051435, dated May 21, 2008.
International Preliminary Report on Patentability for corresponding International Application No. PCT/US08/51435 (Jul. 21, 2009).

* cited by examiner

Primary Examiner — Xuan Thai
Assistant Examiner — Alvin Carlos
(74) Attorney, Agent, or Firm — Marshall, Gerstein & Borun LLP; Michael P. Furmanek

(57) ABSTRACT

A breathing apparatus simulator unit (BASU) comprises a mouthpiece/noseclip subassembly and a cartridge subassembly. The mouthpiece/noseclip subassembly includes the same mouthpiece/noseclip subassembly that is utilized in an actual self-contained self-rescuer (SCSR) device. The cartridge subassembly comprises a container containing a reactionary material. The reactionary material reacts with at least one product of a user's exhalation to generate heat and resistance, thereby providing sensations to simulate the use of an actual SCSR.

26 Claims, 5 Drawing Sheets

BREATHING APPARATUS SIMULATOR

CROSS-REFERENCE TO RELATED APPLICATIONS

The benefit of priority of U.S. Provisional Patent Application No. 60/885,821, filed Jan. 19, 2007, is hereby claimed, and the entire contents thereof are incorporated herein by reference.

FIELD OF THE INVENTION

Present invention generally relates to breathing apparatus simulators and, more particularly, to breathing apparatus simulators for simulating self-contained self-rescuer breathing apparatuses adapted for use in situations where temporary respiratory relief is desired.

BACKGROUND

Mining operations involving coal, iron ore, copper, and/or other materials include dangerous activities. These operations require miners to enter subterranean mines and perform various arduous mining activities. Such subterranean mines have limited oxygen due to their isolation from earth's outside atmosphere. Accordingly, one risk involved with such operations includes the potential for fires within the mine. Even a small fire can consume the limited oxygen supply within the mine and emit enough smoke to seriously harm the miners within the mine whom may not be able to exit the mine fast enough.

One known means for alleviating such a risk includes the provision of Self-Contained Self-Rescuer (SCSR) devices within the mine. Common SCSR's include closed-loop breathing apparatus comprising a mask, a mouthpiece, and/or a nose-piece, an inlet fluidly coupled to a container containing a small amount of breathable air, i.e., oxygen, and an outlet coupled to a carbon dioxide scrubber. When donned by a miner, such known SCSR's may provide the miner with breathable air for a fixed time period, thereby allowing the miner to safely exit the mine to minimize risk of suffocation due to smoke inhalation or lack of oxygen.

One concern arising with the use of SCSR's is that miners are not familiar with how the SCSR operates. More particularly, miners may not know what to expect when donning and breathing with the SCSR. For example, as mentioned, typical SCSR's include closed-loop systems comprising a breathing apparatus coupled to both a supply of breathable air and a carbon dioxide scrubbing device. The carbon dioxide scrubbing device tends to increase the temperature of the recycled breathable air. Therefore, during use, the sensation felt by the user may include a rise in the temperature of the breathable air, as well as resistance to the normal flow of breath. It is conceivable, for example, that a user who is not familiar with the SCSR may think that these sensations mean that the SCSR is malfunctioning. Alternatively, these sensations may cause a user to be frightened and panic. In either situation, the user may be tempted to remove and discard the SCSR, thereby placing him or herself in danger.

Accordingly, an important aspect of providing SCSR's within mines includes training miners and other mine personnel on the proper operation and utilization of the SCSR's. The Mine Safety and Health Administration (MSHA) requires that each miner undergo annual expectation training. However, it may not be cost-effective to perform such training with the actual commercialized SCSR devices that are provided in the mines. Therefore, the training allows for each miner to undergo annual training that includes breathing through a realistic Self-Contained Self-Rescuer (SCSR) "training unit" that simulates the sensation of the breathing resistance and heat generated by an actual SCSR.

SUMMARY

One aspect of the present disclosure provides a breathing apparatus simulator unit (BASU) comprising a mouthpiece/noseclip subassembly and a cartridge subassembly. In one form, the mouthpiece/noseclip subassembly includes the same mouthpiece/noseclip subassembly that is utilized in an actual Self-Contained Self-Rescuer (SCSR) device. The cartridge subassembly comprises a container for containing a reactionary material. The reactionary material reacts with at least one product of a user's exhalation to generate heat and resistance, thereby providing sensations to simulate the use of an actual SCSR.

DETAILED DESCRIPTION

Figure 1:
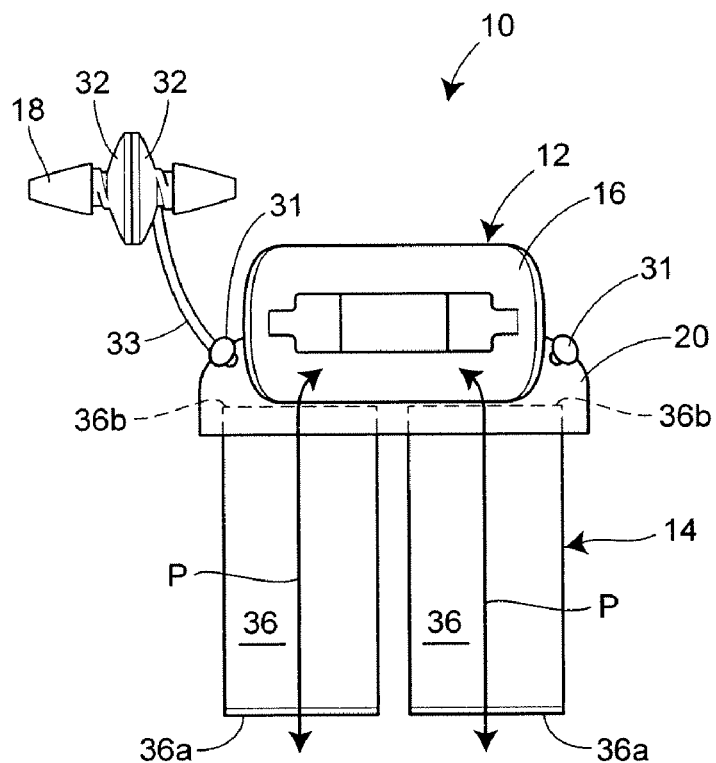
FIG. 1 is a front elevational view of one embodiment of a breathing apparatus simulator unit (BASU) constructed in accordance with the principles of the present invention.
Figure 2:
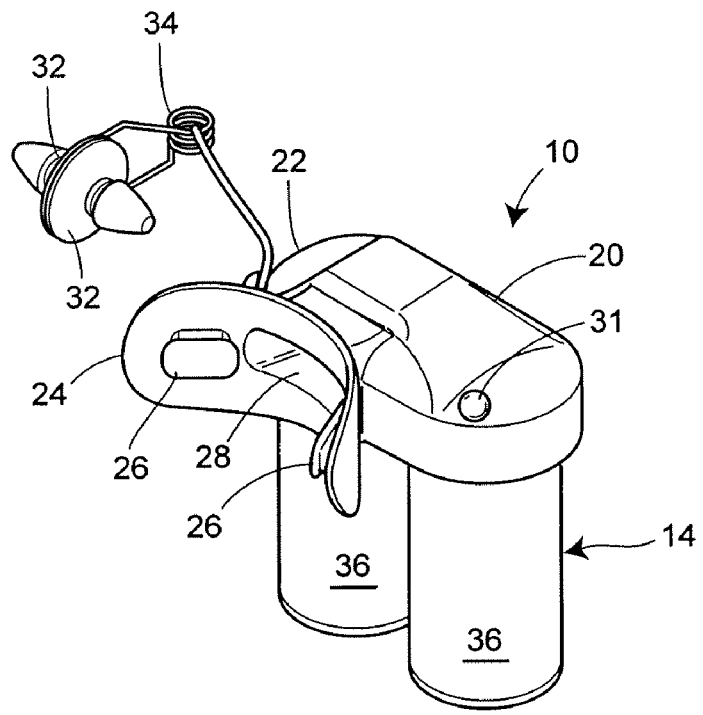
FIG. 2 is a perspective view of the BASU of FIG. 1.

FIGS. 1 and 2 depict one embodiment of a breathing apparatus simulator unit (BASU) 10 constructed in accordance with the present invention. The BASU 10 comprises a two-part open-circuit breathing apparatus assembly including a mouthpiece/noseclip subassembly 12 and a cartridge subassembly 14.

The mouthpiece/noseclip subassembly 12 comprises a mouthpiece 16 and a noseclip 18. In the disclosed embodiment, the mouthpiece 16 comprises the same mouthpiece as is utilized in actual commercialized versions of the Self-Contained Self-Rescuer (SCSR) devices. One advantage of using the same mouthpiece 16 as is used in the actual SCSR's is that the user of the BASU becomes familiar with the appearance and general feel of the mouthpiece 16.

The mouthpiece 16 comprises a housing component 20, a conduit 22, a lip guard 24, and a pair of bite guards 26. Additionally, the mouthpiece 16 is constructed to define a flow path that fluidly couples an opening 28 in the lip guard 24 with the housing component 20, which contains the cartridge subassembly 14, via the conduit 22. Therefore, during use, a user positions the mouthpiece adjacent one's mouth and bites the bite guards 26 in a manner that is generally well known.

Figure 3:
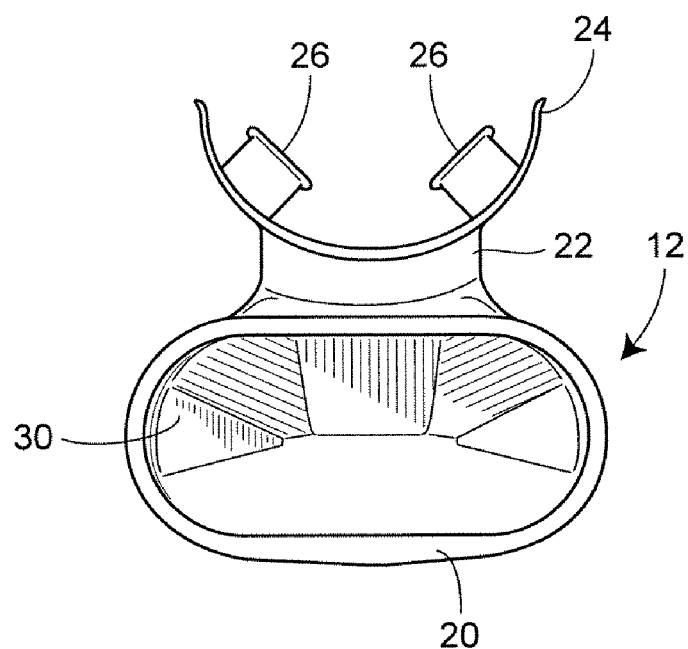
FIG. 3 is a bottom view of a mouthpiece component of the BASU of FIGS. 1 and 2.

As depicted in FIG. 3, the housing component 20 has a generally racetrack shaped cross-section (or top/bottom plan view) and defines an opening 30 for receiving the cartridge subassembly 14. In the disclosed embodiment, the opening 30 transitions into a truncated pyramid-shaped cavity within the housing component 20. Such cavity lends to an efficient flow of air through the mouthpiece 16. Moreover, the housing component 20 comprises a pair of cleats 31, as depicted in FIGS. 1 and 2. The cleats 31 are adapted to retain a tether or strap 33 for mechanically connecting the noseclip 18 to the mouthpiece 16. In one embodiment, the mouthpiece 16 is constructed of a material such as a plastic, rubber, or some similarly functional material.

The noseclip 18, as depicted in FIGS. 1 and 2, comprises a pair of nosepads 32 and a spring 34. The spring 34 of the disclosed embodiment comprises a torsion spring mechanically coupling the nosepads 32 and biasing the nosepads 32 together. Accordingly, upon a user donning the noseclip 18, the nosepads 32 compress the nostrils to seal the nasal cavity off from the atmosphere, thereby restricting any breathing to be performed through the mouth.

Figure 5:
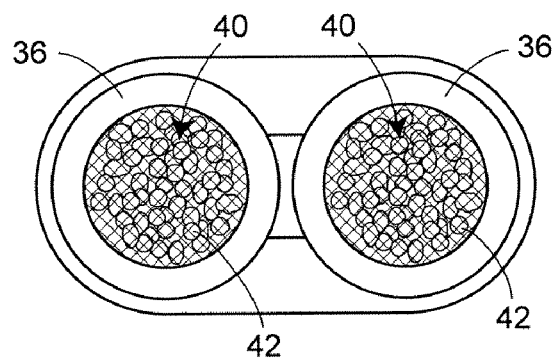
FIG. 5 is a bottom view of the cartridge subassembly of the BASU of FIG. 4.
Figure 6:
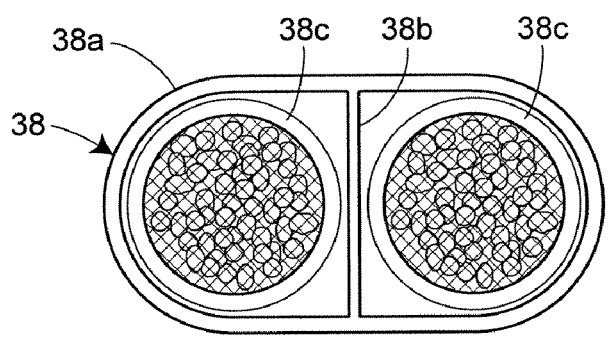
FIG. 6 is a top view of the cartridge subassembly of the BASU of FIGS. 4 and 5.

The cartridge subassembly 14 comprises a double-barreled assembly including a pair of canisters 36 and a coupler 38. As illustrated in FIG. 1, for example, the canisters 36 are hollow cylindrical canisters having first open ends 36a and second open ends 36b. The first open ends 36a define openings that are in direct fluid communication with the atmosphere. That is, the first open ends 36a communicate with the atmosphere without interference, obstruction, or interruption from other components of the device, or otherwise. The second open ends 36b define openings in fluid communication with the coupler 38. So configured, the canisters 36 define flow paths P extending from the atmosphere and the mouthpiece 16 between the first and second open ends 36a, 36b, thereby defining an open-circuit breathing apparatus and enabling a user to inhale and exhale through the canisters 36. The canisters 36 are substantially completely filled with a reactionary material 40 (shown in FIG. 5, for example), which is retained therein with steel top and bottom screens 42 disposed adjacent the first and second open ends 36a, 36b. FIG. 5 only depicts the bottom screens 42. FIG. 6 depicts the top screens 42. The reactionary material 40, which will be described in more detail below, enables the BASU 10 to provide sensations to the user that substantially simulate the sensations experienced when using an actual SCSR.

Figure 4:
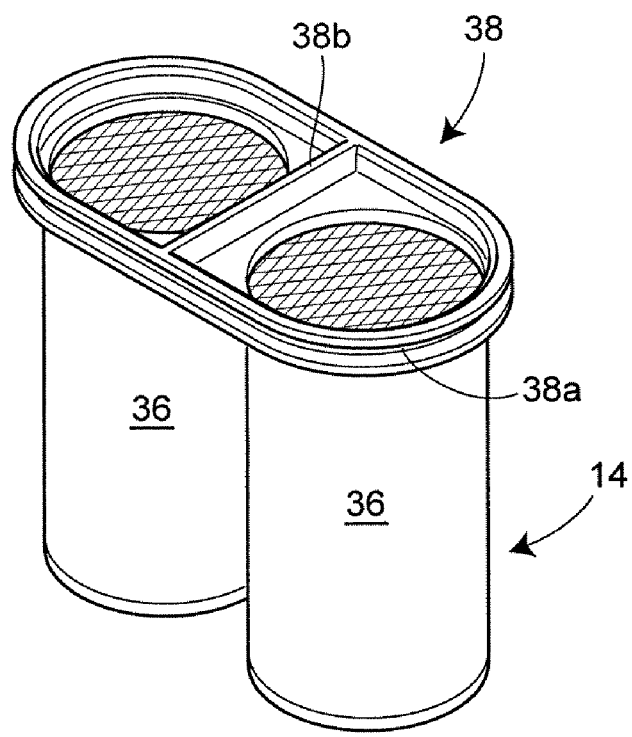
FIG. 4 is a perspective view of a cartridge subassembly of the BASU of FIGS. 1 and 2.

Referring back to FIG. 4, the canisters 36 are constructed of paper, cardboard, chipboard, plastic, or any other material capable of serving the principles of the present disclosure. For example, in one embodiment, the canisters 36 are constructed of a material that serves as an insulator to retain heat during use of the BASU 10 to thereby maximize the efficiency at which the BASU 10 simulates an actual SCSR. The coupler 38 is constructed of plastic, for example, and comprises a ring portion 38a and a truss portion 38b, as depicted in FIGS. 4 and 6. The outside of the ring portion 38a is sized and configured similar to the opening 30 in the housing component 20 of the mouthpiece 16 such that the coupler 38 may frictionally be retained therein. The truss portion 38b extends across a midportion of the inside of the ring portion 38a and, in combination with the ring portion 38a, defines a pair of circular openings 38c (shown in FIG. 6) for receiving and retaining the canisters 36. In one embodiment, the canisters 36 are frictionally retained within the coupler 38. In another embodiment, the canisters 36 are retained within the coupler with an adhesive such as glue. Accordingly, the coupler 38 frictionally retains the canisters 36 within the housing component 20 of the mouthpiece 16, as depicted in FIG. 2. Accordingly, with the cartridge subassembly 14 attached to the mouthpiece 16, a user may use the BASU 10 during expectation training.

As mentioned above, the canisters 36 contain a reactionary material 40. In one embodiment, this reactionary material 40 is porous and formulated such that it provides both an increase in temperature of the breathing air and resistance to the flow of the breathing air through the BASU 10. In one embodiment, the reactionary material 40 comprises a non-hazardous and non-corrosive material that reacts exothermically with at least one product of exhalation, i.e., $H_2O$, $CO_2$, $O_2$, etc. A non-hazardous material is defined herein as a material that has not been assigned a UN or an NA number classifying it as a hazardous chemical and/or material. Preferably, the reactionary material 40 completely consists of a non-hazardous material that reacts exothermically with water vapor during a user's exhalation. For example, during use, when a user exhales through the reactionary material 40, a chemical reaction causes the reactionary material 40 to generate heat. Therefore, upon inhalation, the heat is picked up by the incoming ambient air to provide the sensation similar to that which would be provided by an actual SCSR, i.e., increased temperature of breathing air. Moreover, because the reactionary material 40 at least partly obstructs the flow path of the breathing, it generates resistance, which also simulates the performance of the actual SCSR.

In one embodiment, the reactionary material 40 completely comprises a molecular sieve desiccant having a 4×8 mesh bead size, which is commercially available from Delta Adsorbents, Division of Delta Enterprises, Inc., of Roselle, Ill., USA. Such a molecular sieve desiccant includes a 4 angstrom nominal pore diameter, a 24% wt. theoretical equilibrium water capacity, 1.5% wt. water content, 1800 BTU/lb H20 maximum heat of adsorption, approximately 0.23 BTU/lb/deg F. specific heat, 18 lbs crush strength, and 2.5-4.5 millimeter nominal commercial bead size. In alternative embodiments, the reactionary material 40 could at least partly comprise other materials such as lithium hydroxide, soda lime, or any other material capable of serving the principles of the present invention. Also, while a molecular sieve desiccant having a 4×8 mesh bead size has been disclosed, other mesh bead sizes can be used. For example, smaller mesh sizes can provide greater breathing resistance, and greater mesh size can provide less breathing resistance. Accordingly, the particular operating characteristics of the resistance can potentially be changed to simulate different breathing conditions or apparatuses.

Figure 7:
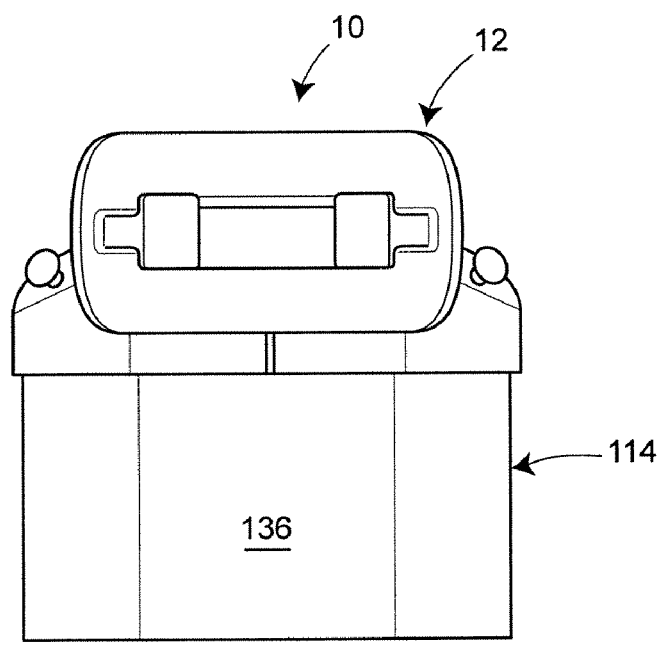
FIG. 7 is a front elevational view of a second embodiment of a BASU constructed in accordance with the principles of the present disclosure.
Figure 8:
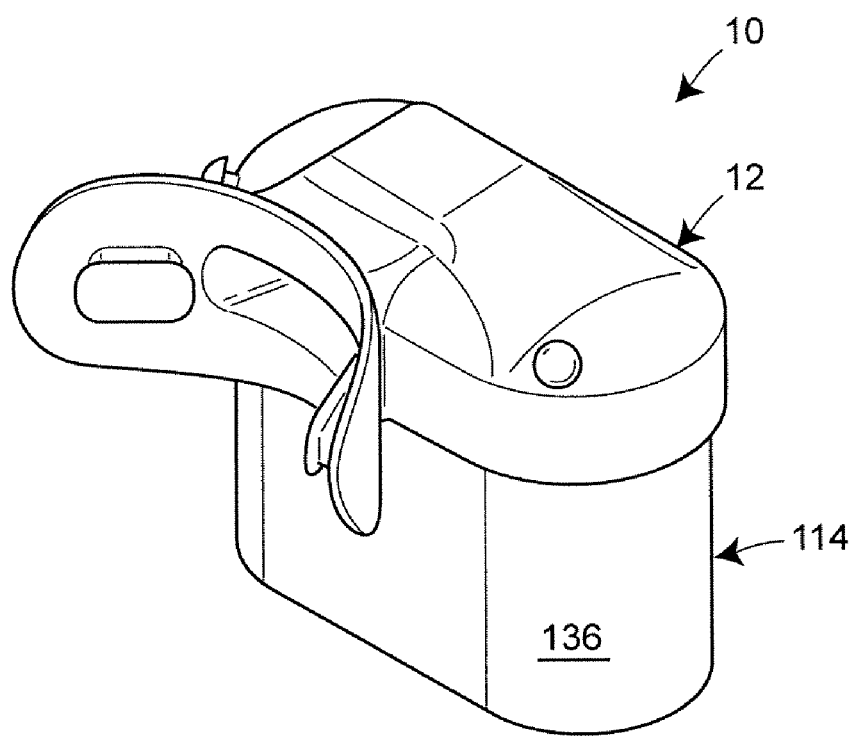
FIG. 8 is a perspective view of the BASU of FIG. 7.
Figure 9:
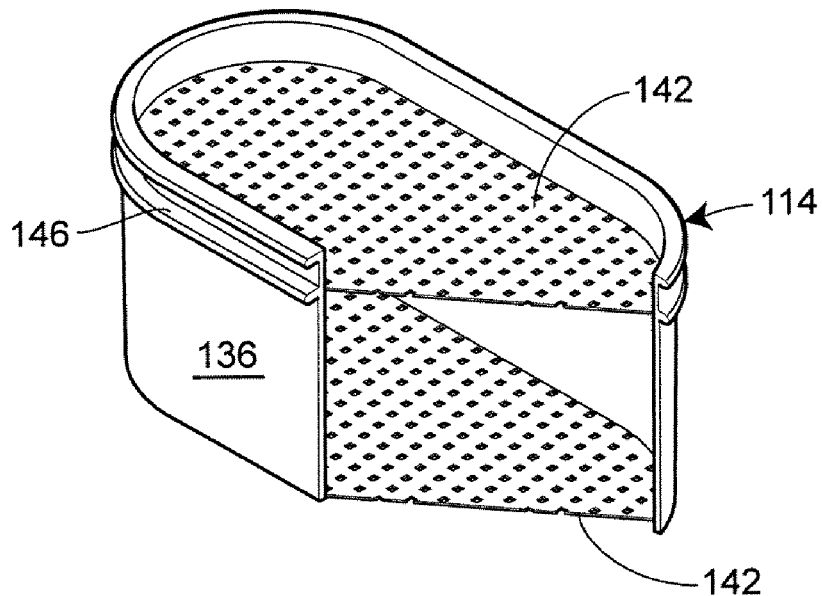
FIG. 9 is a partially cut-away perspective view of a cartridge subassembly of the BASU of FIGS. 7 and 8.

While the BASU 10 has been described thus far as comprising a double-barreled cartridge subassembly 14, alternative embodiments may comprise other configurations. For example, FIGS. 7 and 8 depict one embodiment of the BASU 10 comprising a mouthpiece/nosepiece subassembly 12 identical to that disclosed with reference to FIGS. 1 and 2, but with an alternative cartridge subassembly 114. Specifically, the cartridge subassembly 114 depicted in FIGS. 7 and 8 comprises a single canister 136 shaped with a racetrack cross-section, similar to the opening 30 (shown in FIG. 3) in the mouthpiece 16. So configured, the canister 136 of the cartridge subassembly 114 may not require a coupler component similar to the coupler 38 described above. Rather, the canister 136 may directly frictionally engage with the opening 30 in the mouthpiece 16. Otherwise the cartridge subassembly 114 depicted in FIGS. 7 and 8 is constructed identical to the cartridge subassembly 14 depicted in FIGS. 1 and 2 and described above. For example, as shown in FIG. 9, the canister 136 includes a generally hollow canister for containing the reactionary material 40 (not shown) and a pair of steel screens 142 for retaining the reactionary material 40 in the canister 136. Moreover, as depicted, the outside surface of the canister 136 includes a bead 146 extending around a top portion thereof. The bead 146 aids in the frictional engagement between the canister 136 and the mouthpiece 16 adjacent the opening 30. The canister 136 may be constructed of any of the materials discussed above with respect to the canisters 36. In a plastic embodiment of the canister 136, the canister may be constructed through an extrusion process.

Figure 10:
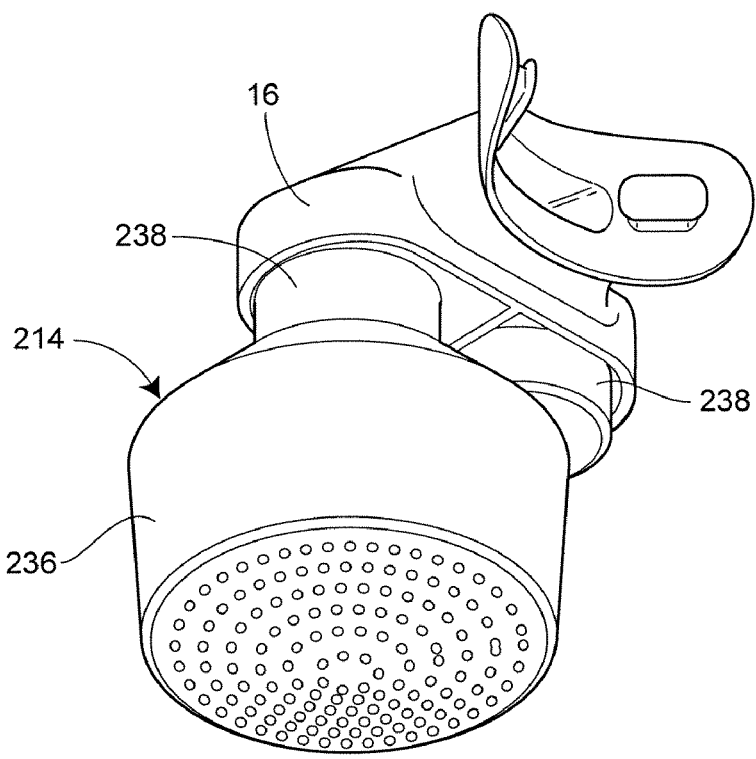
FIG. 10 is a perspective view of a third embodiment of a BASU constructed in accordance with the principles of the present disclosure.
Figure 11:
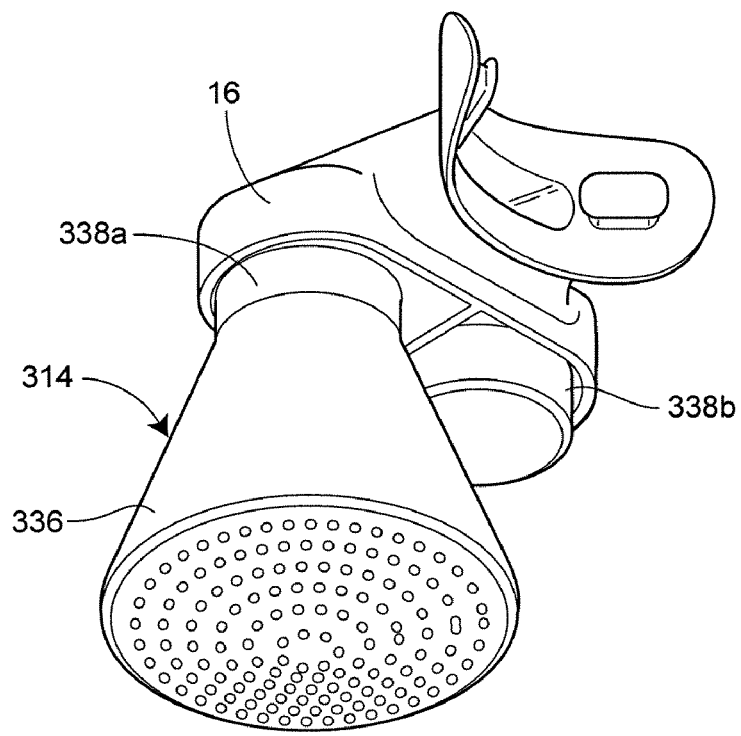
FIG. 11 is a perspective view of a fourth embodiment of a BASU constructed in accordance with the principles of the present disclosure.

In light of the foregoing, it should be appreciated that the cartridge subassembly 14, 114 need not take any specific shape or form, but rather, may be designed as desired. For example, while the cartridge subassembly 14 depicted in FIGS. 1 and 2 includes a pair of generally cylindrical canisters 36, and the cartridge subassembly 114 depicted in FIGS. 7 and 8 includes a generally racetrack shaped canister 136, alternative embodiments can take any shape and configuration. For example, FIG. 10 illustrates a cartridge subassembly 214 including a single cylindrical canister 236 co-molded with a pair of conduit portions 238. The pair of conduit portions 238 may therefore attach to the mouthpiece 16 via a coupler (not shown), which is similar to the coupler 38 disclosed and described above with reference to FIGS. 4 and 6. Moreover, FIG. 11 depicts another alternative embodiment of a cartridge subassembly 314 comprising a single frustoconically-shaped canister 336 co-molded with first and second conduit portions 338a, 338b. The first conduit portion 338a is coupled directly with the canister 336 and in fluid communication between the canister 336 and the mouthpiece 16. The second conduit portion 338b is disposed beside the first conduit portion 338a and may be adapted to be closed, or to receive a valve, or some other apparatus for some other use. Nevertheless, it should be appreciated that the shape and configuration of the cartridge subassemblies 14, 114, 214, 314 may be varied, as desired for any particular use. In any such configuration, the cartridge subassembly 14, 114, 214, 314 still contains the reactionary material 40. Furthermore, each of the canisters 236, 336, of the subassemblies 214, 314, respectively, comprise at least co-molded screens (illustrated on the bottom side thereof) and potentially co-molded top-screens (not shown) instead of the steel screens discussed above with canisters 36 and 136.

Furthermore, while the cartridge subassemblies 14, 114, 214, 314 have been disclosed herein as being used with the mouthpiece 16 particularly depicted and described, it should be appreciated that the cartridge subassemblies 14, 114, 214, 314 may be adapted to be used with any design of mouthpiece subassembly. The scope of the present invention, and thus, this disclosure is not limited to the particular mouthpiece subassembly disclosed herein. In this regard, the cartridge subassembly 14, 114, 214, 314 may be offered without the mouthpiece subassembly and alternatively, with an adapter component that serves to mechanically adapt the cartridge subassembly 14, 114, 214, 314 to different mouthpiece subassemblies available on the market.

Further still, in a preferred embodiment, the BASU 10 constructed in accordance with the principles of the present invention can further be equipped with a filter (not shown) disposed between the top screen 42 (FIG. 6) and the mouthpiece 16. The filter can serve to capture nuisance dust that can accumulate within the cartridge subassembly 14, 114, 214, 314, for example, such that a user does not inhale the same. In one embodiment, the filter can comprise a permanently charged electrostatic polypropylene web situated immediately adjacent the top screen 42. Such filters typically have higher efficiencies with lower pressure drop compared to purely mechanical filter media. Nevertheless, alternative embodiments of the BASU 10 can include filters of different materials such as those constructed of fiberglass, for example, or no filter at all.

In light of the foregoing, it should be appreciated that a breathing apparatus simulator constructed in accordance with the embodiments disclosed herein provides a cost-effective simulator that allows for easy replacement and disposal of spent cartridge subassemblies 14. Specifically, after a user uses a cartridge subassembly 14 during a training operation, the spent cartridge subassembly 14 can simply be removed from the mouthpiece 16 and replaced with a new cartridge subassembly 14.

Additionally, when using the preferred embodiment of the spent cartridge subassembly 14, which includes only non-hazardous reactionary material 40, the spent cartridge subassembly 14 can be discarded into a standard trash can. When the cartridge subassembly 14 includes hazardous reactionary material 40, the cartridge subassembly 14 must be discarded in accordance with disposal standards for hazardous waste.

Other advantages realized in using only non-hazardous reactionary material 40 are that the user of the breathing apparatus simulator unit 10 is absolutely free from inhaling hazardous and/or corrosive gases and/or dusts. Further, shipping and manufacturing costs associated with non-hazardous materials are generally less than those costs associated with hazardous material.

Finally, it should be appreciated that the various embodiments described herein are merely examples of what the inventor considers the invention, which is defined by the spirit and scope of the following claims.

What is claimed:

1. A breathing apparatus, comprising:
   a mouthpiece;
   a canister removably attached to the mouthpiece, the canister defining a first open end in direct fluid communication with the atmosphere, a second open end opposite the first open end and in fluid communication with the mouthpiece, and a flowpath extending between the first and second open ends, the flow path providing fluid communication between the mouthpiece and the atmosphere; and
   a reactionary material disposed in the canister and extending from the first open end to the second open end for reacting with at least one product of a user's exhalation to generate heat and resistance sensations to the user, thereby simulating the use of an actual self-contained self-rescuer device, the entirety of the reactionary material being a molecular sieve dessicant.

2. The apparatus of claim 1, wherein the molecular sieve dessicant comprises a plurality of beads.

3. The apparatus of claim 1, wherein the molecular sieve dessicant is non-hazardous.

4. The apparatus of claim 1, wherein the molecular sieve dessicant comprises a nominal pore diameter of approximately 4 angstrom.

5. The apparatus of claim 1, wherein the molecular sieve dessicant comprises a maximum heat of adsorption of 1800 BTU/lb H2O.

6. The apparatus of claim 1, wherein the molecular sieve dessicant reacts exothermically with H2O.

7. The apparatus of claim 1, further comprising bottom and top screens disposed adjacent the first and second open ends, respectively, of the canister and retaining the molecular sieve dessicant within the canister.

8. The apparatus of claim 7, wherein each screen comprises a steel mesh material.

9. The apparatus of claim 1, wherein the canister is constructed of a thermally insulating material.

10. The apparatus of claim 9, wherein the canister is constructed of one of a plastic material, a paper material, a cardboard material, and a chipboard material.

11. A breathing apparatus, comprising:
   a mouthpiece;
   a canister removably attached to the mouthpiece, the canister providing fluid communication between a first open end of the canister in communication with the atmosphere and a second open end of the canister in communication with the mouthpiece, the second open end opposite the first open end; and
   a means for generating heat and resistance sensations to a user in response to a user's exhalation to simulate the use of an actual self-contained self-rescuer device, the means for generating heat and resistance disposed within the canister and extending from the first open end to the second open end, the entirety of the means for generating heat and resistance being non-hazardous molecular sieve dessicant.

12. The apparatus of claim 11, wherein the non-hazardous means comprises a plurality of beads.

13. The apparatus of claim 11, wherein the non-hazardous means comprises a nominal pore diameter of approximately 4 angstrom.

14. The apparatus of claim 11, wherein the non-hazardous means comprises a maximum heat of adsorption of 1800 BTU/lb H2O.

15. The apparatus of claim 11, wherein the non-hazardous means reacts exothermically with H2O.

16. The apparatus of claim 11, further comprising bottom and top screens disposed adjacent the first and second open ends, respectively, of the canister and retaining the non-hazardous means within the canister.

17. The apparatus of claim 16, wherein each of the screens comprises a steel mesh material.

18. The apparatus of claim 11, wherein the canister is constructed of a thermally insulating material.

19. The apparatus of claim 11, wherein the canister is constructed of one of a plastic material, a paper material, a cardboard material, and a chipboard material.

20. A breathing apparatus, comprising:
   a mouthpiece;
   a canister removably attached to the mouthpiece, the canister defining a first open end in direct fluid communication with the atmosphere, a second open end opposite the first open end and in fluid communication with the mouthpiece, and a flowpath extending between the first and second open ends, the flow path providing fluid communication between the mouthpiece and the atmosphere;
   a reactionary material disposed within the canister and extending from the first open end to the second open end for reacting with at least one product of a user's exhalation to generate heat and resistance, thereby providing heat and resistance sensations to the user that simulate the use of an actual self-contained self-rescuer device, the entirety of the reactionary material being one of a hazardous material and a non-hazardous molecular sieve dessicant.

21. The apparatus of claim 20, wherein the reactionary material comprises a plurality of beads.

22. The apparatus of claim 20, wherein the reactionary material reacts exothermically with H2O.

23. The apparatus of claim 20, further comprising bottom and top screens disposed adjacent the first and second open ends, respectively, of the canister and retaining the reactionary material in the canister.

24. The apparatus of claim 23, wherein each of the screens comprises a steel mesh material.

25. The apparatus of claim 20, wherein the canister is constructed of a thermally insulating material.

26. The apparatus of claim 25, wherein the canister is constructed of one of a plastic material, a paper material, a cardboard material, and a chipboard material.

* * * * *